(12) United States Patent
Brinker et al.

(10) Patent No.: US 10,321,853 B2
(45) Date of Patent: Jun. 18, 2019

(54) EVALUATION OF THE POSITIONING OF AN EXAMINATION OBJECT

(71) Applicants: Gerhard Brinker, Erlangen (DE); Franz Hebrank, Herzogenaurach (DE); Patrick Sieber, Aurachtal (DE)

(72) Inventors: Gerhard Brinker, Erlangen (DE); Franz Hebrank, Herzogenaurach (DE); Patrick Sieber, Aurachtal (DE)

(73) Assignee: Siemens Healthcare GmbH, Erlangen (DE)

(*) Notice: Subject to any disclaimer, the term of this patent is extended or adjusted under 35 U.S.C. 154(b) by 129 days.

(21) Appl. No.: 15/409,759

(22) Filed: Jan. 19, 2017

(65) Prior Publication Data
US 2017/0205478 A1 Jul. 20, 2017

(30) Foreign Application Priority Data
Jan. 19, 2016 (DE) .................. 10 2016 200 611

(51) Int. Cl.
*A61B 5/055* (2006.01)
*A61B 5/107* (2006.01)
(Continued)

(52) U.S. Cl.
CPC .......... *A61B 5/1079* (2013.01); *A61B 5/0555* (2013.01); *A61B 5/1077* (2013.01); *G01R 33/283* (2013.01); *G16H 40/63* (2018.01)

(58) Field of Classification Search
CPC .... G01R 33/30; G01R 33/385; G01R 33/546; A61B 5/0555; A61B 5/1077; A61B 5/1079; G01B 15/00
(Continued)

(56) References Cited

U.S. PATENT DOCUMENTS

2003/0098688 A1 5/2003 Brinker et al.
2005/0265516 A1 12/2005 Haider
(Continued)

FOREIGN PATENT DOCUMENTS

DE 102004024097 A1 12/2005
DE 102007011695 A1 9/2008
(Continued)

OTHER PUBLICATIONS

German Office Action for German Application No. 10 2016 200 611.8, dated Sep. 28, 2016, with English Translation.
(Continued)

*Primary Examiner* — Susan S Lee
(74) *Attorney, Agent, or Firm* — Lempia Summerfield Katz LLC

(57) ABSTRACT

A method for evaluating positioning of an examination object on a patient-positioning apparatus in a magnetic resonance unit, a magnetic resonance unit, and a computer program product are provided. The method includes acquiring positioning data relating to the examination object using an acquisition unit. Using the acquired positioning data, positioning information relating to the examination object is determined using an analysis unit. Evaluation information is determined using the positioning information, using an evaluation unit. Using the evaluation information, an evaluation signal is transmitted using an output unit. Monitoring of a specific absorption rate may be adjusted using the evaluation signal.

19 Claims, 3 Drawing Sheets

(51) Int. Cl.
*G01R 33/28* (2006.01)
*G16H 40/63* (2018.01)

(58) Field of Classification Search
USPC .......................................................... 324/322
See application file for complete search history.

(56) References Cited

U.S. PATENT DOCUMENTS

| | | |
|---|---|---|
| 2008/0218166 A1 | 9/2008 | Arnold |
| 2011/0043205 A1* | 2/2011 | Graesslin ........... G01R 33/5612 324/307 |
| 2013/0261428 A1 | 10/2013 | Blumhagen et al. |
| 2014/0077811 A1* | 3/2014 | Lin ........................ A61B 5/055 324/309 |
| 2015/0338478 A1* | 11/2015 | Schillak ............. G01R 33/3607 324/309 |
| 2015/0343237 A1* | 12/2015 | Hausotte ................ A61B 90/39 600/411 |
| 2017/0000446 A1 | 1/2017 | Brinker et al. |

FOREIGN PATENT DOCUMENTS

| | | |
|---|---|---|
| DE | 10150138 B4 | 10/2009 |
| DE | 102012205236 A1 | 10/2013 |
| WO | WO2014064553 A1 | 5/2014 |

OTHER PUBLICATIONS

Ingmar Graesslin: "Monitoring Safety and RF Heating for Parallel Transmission Systems", Philips Research Europe—Hamburg, ISMRM Workshop on MR Safety: RF Heating of the Human in MRI, 2010.

* cited by examiner

EVALUATION OF THE POSITIONING OF AN EXAMINATION OBJECT

This application claims the benefit of DE 10 2016 200 611.8, filed on Jan. 19, 2016, which is hereby incorporated by reference in its entirety.

BACKGROUND

The present embodiments relate to evaluating a positioning of an examination object on a patient-positioning apparatus in a magnetic resonance unit.

Magnetic Resonance Imaging (MRI) is a known technique for generating internal images of the body of an examination object. For this purpose, typically rapidly switched gradient pulses are superimposed on a static constant magnetic field in a magnetic resonance unit. The pulses are generated by a gradient system of the magnetic resonance unit. In order to trigger magnetic resonance signals, radio frequency excitation pulses are radiated into the examination object by a radio frequency antenna unit of the magnetic resonance unit, and the magnetic resonance signals triggered are captured. Based on this, magnetic resonance images are created.

When carrying out magnetic resonance imaging, an inadequate positioning of the examination object on a patient-positioning apparatus of the magnetic resonance unit may occur, leading to an adverse effect on the examination object (e.g., burns).

SUMMARY AND DESCRIPTION

The scope of the present invention is defined solely by the appended claims and is not affected to any degree by the statements within this summary.

The present embodiments may obviate one or more of the drawbacks or limitations in the related art. For example, the positioning of the examination object is monitored, such that an unfavorable positioning is avoided.

Accordingly, a method for evaluating a positioning of an examination object on a patient-positioning apparatus in a magnetic resonance unit includes acquiring positioning data for the examination object using an acquisition unit. Using the acquired positioning data, positioning information for the examination object is determined using an analysis unit. Evaluation information is determined by the positioning information using an evaluation unit. Using the evaluation information, an evaluation signal is transmitted by an output unit.

The examination object (e.g., a human or animal patient) may be placed on the patient-positioning apparatus or places itself on the patient-positioning apparatus prior to the acquisition of the positioning data (e.g., in the course of preparations for a measurement).

The evaluation signal may include a warning signal that is able to indicate an unfavorable positioning of the examination object, such that injuries to the examination object may be avoided.

The method may be carried out a plurality of times in succession. As a result thereof, the evaluation signal may be updated from time to time. For example, a dynamic evaluation of the positioning of the examination object is possible, such that, for example, a movement of the examination object may also be taken into account.

In one embodiment, the positioning information includes contour information relating to at least one part of the examination object. Contour information may include at least information about a contour (e.g., about a profile and/or geometry and/or shape of the examination object). The contour information may be determined by the shape of the examination object and by a position of the examination object on the patient-positioning apparatus.

Typically, the examination object includes a plurality of parts of the body. In one embodiment, the contour information includes information on a relative position of at least two parts of the plurality of parts of the body. For example, the contour information describes a possible contact between a leg (e.g., a thigh and/or a knee and/or a lower leg and/or a foot) and another leg, and/or between an arm and another arm (e.g., by hands that are folded). The contour information may also describe, for example, a possible contact between a leg and/or arm and a different part of the examination object. Consequently, the contour information may include information from which the presence of a possible current loop, referred to hereinafter for short as a loop, may be deduced. This is advantageous since loops may lead to injuries of the examination object.

According to a further aspect of the method, the positioning information includes positioning information for at least one part of the examination object. For example, the positioning information includes a relative position of the examination object on the patient-positioning apparatus.

In other words, the contour information may include information as to how the examination object is positioned on the patient-positioning apparatus, while the positioning information may describe where the examination object is positioned on the patient-positioning apparatus. Valuable information may be deduced from the positioning information. For example, potential safety margins for carrying out a measurement may be minimized the more precisely the position of the examination object relative to a transmission coil may be determined.

In most cases, the magnetic resonance unit includes a patient-accommodating region that is delimited by an inside wall. In one embodiment, the positioning information includes a minimum distance between the examination object and the inner wall. For example, a distance between the examination object and a transmission coil (e.g., a body coil) may be determined therefrom.

One embodiment makes provision for the acquisition of the positioning data relating to the examination object to ensue during a movement of the patient-positioning apparatus. For example, the positioning data may be acquired during a procedure in which the patient-positioning apparatus slides into a patient-accommodating region of the magnetic resonance unit. For example, an alignment may also be made. As a result thereof, a positioning may be evaluated in an efficient manner.

One embodiment of the method makes provision for the positioning data to be acquired by optical signals. The optical signals may be acquired using at least one camera, for example.

Optical signals may be electromagnetic signals in a wavelength range of between 100 nm and 1 mm, for example, as signals in a wavelength range for visible light and/or infrared radiation.

Optical acquisition of the examination object is particularly simple because positioning information may be derived from optical signals in a simple manner. Cameras may be favorably priced and have been technically perfected.

In one embodiment, the magnetic resonance unit includes a magnet unit and a patient-accommodating region. The patient-accommodating region may be surrounded by the magnet unit. The at least one camera may be arranged outside the patient-accommodating region and/or inside the patient-accommodating region and/or inside the magnet unit. For example, the at least one camera may be incorporated in an inside wall (e.g., in an internal tunnel wall) and/or in a cover for the magnet.

A further embodiment of the method makes provision for the acquisition of the positioning data to ensue using magnetic resonance signals. The magnetic resonance signals may be captured using a radio frequency antenna unit that is encompassed by the magnetic resonance unit.

From the magnetic resonance signals, images from which the positioning information may be deduced may, for example, be reconstructed.

For example, the acquisition of the positioning data relating to the examination object may ensue during measurement data capture in magnetic resonance imaging. Consequently, the acquisition may ensue in an efficient manner, since, for example, no potential time-consuming additional steps are necessary.

A further embodiment makes provision for the acquisition of the positioning data to ensue using characteristic radio frequency parameters (RF parameters). The characteristic RF parameters may include coil properties that may be influenced by the examination object. The coil properties may be properties of at least one coil (e.g., of a transmission coil such as a body coil) that are encompassed by the magnetic resonance unit.

The influencing of the coil properties may be detected, for example, with the aid of what are known as scatter parameters and/or of reflection. In addition, the magnetic resonance unit may include pickup coils with which a signal pathway in a transmission coil, in transmission structures (e.g., transmission rods) of the transmission coil may be acquired and compared with a targeted signal pathway. If the patient moves, then the coil properties (e.g., the load properties of the coil) will change, since a coupling generally exists between the coil and the examination object. The movement may then be detected by the change in the reflection properties and/or scatter parameters. The deviation in the signal pathway detected online via pickup coils from the targeted signal pathway may be used as an indicator of movement and in some cases of a permanent change in positioning. This may then trigger a fresh determination of the position.

In one embodiment, positioning information is determined using segmentation and/or pattern recognition. With these methods, a contour of at least one part of the examination object (e.g., possible parts of the body such as extremities of the examination object) may, for example, be detected. As a result thereof, an absolute position of one or of a plurality of parts of the body on the patient-positioning apparatus may be established, for example.

A size and/or a weight of the examination object may be determined after a successful segmentation and/or a pattern recognition. Thus, for example, any inputs from an operator may be monitored.

One embodiment makes provision for the evaluation signal to include positive or negative release information.

Thus, for example, it is only after the detection and checking of a positioning (e.g., of a position) of the examination object (e.g., taking into account specific parts of the body of the examination object such as the torso, head, and/or extremities) and/or after determining and/or checking a minimum distance from an inside wall (e.g., a tunnel inside wall) of the magnetic resonance unit that the capture of measurement data relating to a magnetic resonance imaging procedure is allowed. Only where the positioning is correct does the evaluation signal therefore include positive release information in this case.

With an incorrect positioning of the examination object, the evaluation signal includes negative release information. In this case, an operator may, for example, be alerted to this by the output of a corresponding output signal. In one embodiment, it is only after a correction of the positioning of the examination object that the capture of measurement data relating to the magnetic resonance imaging procedure may be started.

In a development, provision is made by the evaluation signal for monitoring of a specific absorption rate (SAR) to be adjusted. By taking into account the positioning of the examination object, increases in performance may be achieved while at the same time remaining within any limiting values for the SAR.

This may be the case, for example, when the examination object (e.g., a human patient) is moved into a patient-accommodating region of the magnetic resonance unit feet first, since then due to greater variation in the patient's body geometry toward the lower extremities, uncertainty regarding a position of the lower extremities is particularly great.

As precise as possible knowledge of a position of the patient's head is an advantage since it is often necessary to adhere to a separate SAR limit for the head.

Through an evaluation of the actual positioning of the examination object, false conclusions may, for example, be drawn due to the plug-in status of a local coil. If, for example, a patient's head is not positioned in a head coil despite a head coil being plugged in, the adjustment of the monitoring of the specific absorption rate ensues according to the actual positioning of the examination object and not by a presumed positioning derived from the plug-in status of the head coil.

For example, for the event that the positioning information includes a minimum distance between the examination object and the inside wall of the magnetic resonance unit, where there is a minimum distance that is not critical with respect to burns, for example, an SAR limit may be lowered accordingly. As a result thereof, increases in performance are possible since the distance from the inside wall is not critical in many examination situations.

In a development, the positioning information includes information on the physiognomy of at least one part of the examination object. The monitoring of a specific absorption rate is dependent on the physiognomy information relating to the examination object.

If, for example, in the analysis of the acquired positioning data, abnormalities of the examination object, such as missing limbs, unusual body measurements and/or unusual body proportions, are detected, an SAR model that usually forms the basis of SAR monitoring is adjusted. By adjusting the SAR model to the actual physiognomy of the examination object, the safety of the examination object may be increased by a more targeted adherence to given limiting values. For example, knowledge of the physiognomy of any parts of the body that are different provides that SAR limiting values may be calculated correctly.

A magnetic resonance unit that is configured to carry out an evaluation of a positioning of an examination object on a patient-positioning apparatus in a magnetic resonance unit is provided.

In one embodiment, the magnetic resonance unit includes: a patient-positioning apparatus for positioning an examination object; an acquisition unit for acquiring positioning data relating to the examination object; an analysis unit for determining positioning information relating to the examination object using the acquired positioning data; an evaluation unit for determining evaluation information using the positioning information; and an output unit to transmit an evaluation signal using the evaluation information.

In a development, the magnetic resonance unit includes a magnet unit, a patient-accommodating region, and at least one camera that is arranged outside the patient-accommodating region and/or inside the patient-accommodating region and/or inside the magnet unit.

In a further development, the magnetic resonance unit includes at least one pickup coil.

The advantages of the magnetic resonance unit according to the present embodiments essentially correspond to the advantages of the method according to the present embodiments for evaluating a positioning of an examination object on a patient-positioning apparatus in a magnetic resonance unit. The advantages have been set out in detail above. Features, advantages or alternative embodiments referred to here may likewise be applied to the other claimed subject matter and vice versa.

In other words, the substantive claims may also be developed with the features that are described or claimed with reference to a method. The respective functional features of the method are configured in this case by respective substantive modules (e.g., by hardware modules such as one or more processors).

In addition, a computer program product that may be loaded directly into a memory (e.g., a non-transitory computer-readable storage medium) of a programmable computation unit of a magnetic resonance unit is provided with programming (e.g., instructions) in order to carry out a method for evaluating a positioning of an examination object on a patient-positioning apparatus in a magnetic resonance unit when the program is run in the computation unit of the magnetic resonance unit.

The computer program product may include software with source code that is to be compiled and linked up or is just to be interpreted, or an executable software code that only is to be loaded into the memory of the computation unit to run the program. With the computer program product, the method according to one or more of the present embodiments may be carried out rapidly, in an identically repeatable and robust manner. The computer program product is configured such that the computer program product may carry out the method acts by the computation unit. In each case, the computation unit includes, for example, a corresponding working memory, a corresponding graphics card or a corresponding logic unit, such that the computation unit may carry out the respective method acts efficiently. The computer program product is stored, for example, on a computer-readable medium or on a network or server, from where the computer program product may be loaded into a processor of the system control unit. Examples of computer-readable media are a DVD, a magnetic tape, or a USB stick, on which electronically readable control data (e.g., software) is stored. One or more of the present embodiments may therefore likewise take the computer-readable medium as a point of departure.

BRIEF DESCRIPTION OF THE DRAWINGS

Components that correspond to one another are denoted by the same reference characters in all the figures.

DETAILED DESCRIPTION

Figure 1:
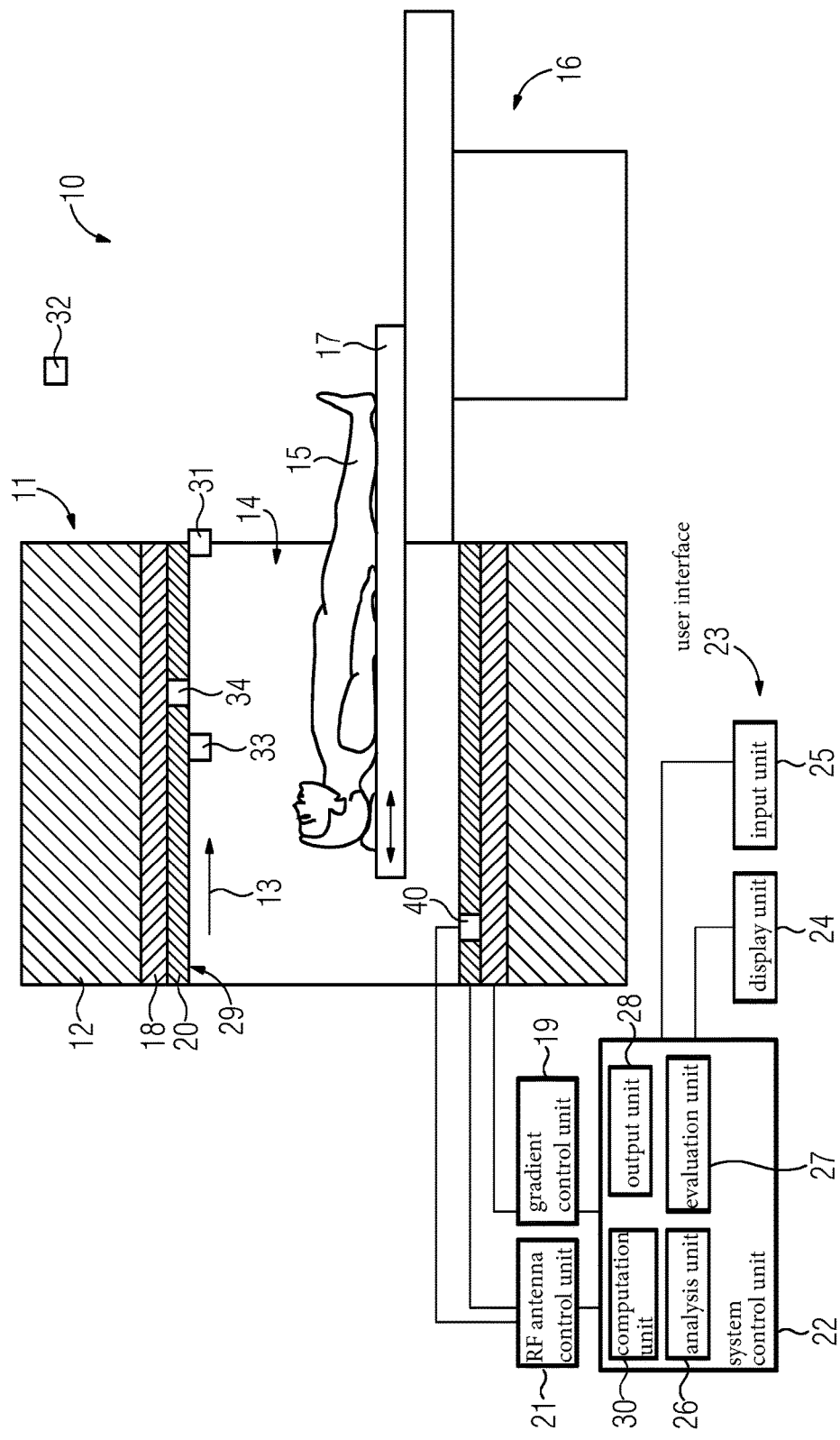
FIG. 1 shows a representation of a magnetic resonance unit.

FIG. 1 shows a diagrammatic view of one embodiment a magnetic resonance unit 10. The magnetic resonance unit 10 includes a magnet unit 11. The magnet unit 11 includes a superconducting main magnet 12 to generate a strong and, for example, a chronologically constant main magnetic field 13. In addition, the magnetic resonance unit 10 includes a patient-accommodating region 14 to accommodate an examination object 15 (e.g., a human patient). The patient-accommodating region 14 is enclosed by an inside wall 29, which, for example, is included by a cover of the magnet unit 11. The patient-accommodating region 14 in the present exemplary embodiment is cylindrical in design and is encompassed circumferentially by the magnet unit 11. Basically, however, a design of the patient-accommodating area 14 that deviates therefrom may be provided. The patient 15 is positioned on a patient-positioning apparatus 16 of the magnetic resonance unit 10. In order to move the patient 15 into the patient-accommodating region 14, the patient-positioning apparatus 16 includes a patient table 17 that is moveably configured within the patient-accommodating region 14.

The magnet unit 11 further includes a gradient coil unit 18 to generate magnetic field gradients that are used for spatial encoding during an imaging procedure. The gradient coil unit 18 is controlled by a gradient control unit 19 of the magnetic resonance unit 10. The magnet unit 11 further includes a radio frequency antenna unit 20, which in the present exemplary embodiment is configured as a body coil that is fixedly incorporated into the magnetic resonance unit 10. The radio frequency antenna unit 20 is configured to excite atomic nuclei that appear in the main magnetic field 13 generated by the main magnet 12. The radio frequency antenna unit 20 is controlled by a radio frequency antenna control unit 21 in the magnetic resonance unit 10 and radiates radio frequency magnetic resonance sequences into an examination area that is essentially formed by a patient-accommodating area of the magnetic resonance unit 10. The radio frequency antenna unit 20 is further configured to receive magnetic resonance signals.

To control the gradient control unit 19 and the radio frequency antenna control unit 21, the magnetic resonance unit 10 includes a system control unit 22. The system control unit 22 centrally controls the magnetic resonance unit 10 by, for example, running a predetermined gradient echo imaging sequence. In addition, the system control unit 22 includes an evaluation unit that is not shown in greater detail to evaluate medical imaging data that has been acquired during the magnetic resonance examination. The magnetic resonance unit 10 includes a user interface 23 that is connected to the system control unit 22. Control data, such as imaging parameters, for example, and also reconstructed magnetic resonance images, may be displayed on a display unit 24 (e.g., on at least one monitor) of the user interface 23 for a medical operator. The user interface 23 further includes an input unit 25, by which the information and/or parameters may be input by the medical operator during a measurement procedure.

In order to carry out a method according to one or more of the present embodiments for evaluating a positioning of the examination object 15 on the patient-positioning apparatus 16 of the magnetic resonance unit 10, the magnetic resonance unit 10 includes an acquisition unit that is configured to acquire positioning data relating to the examination object. The acquisition unit may include the radio frequency antenna unit 20 and/or one or a plurality of cameras 31, 32, 33, 34 and/or one or a plurality of pickup coils 40. The radio frequency antenna unit 20 may be configured to acquire magnetic resonance signals as possible positioning data. The cameras 31, 32, 33, 34 may be configured to acquire optical signals as positioning data and may be arranged in different ways. For example, the camera 34 is arranged inside the magnet unit 11, the camera 33 is arranged inside the patient-accommodating region 14, and the camera 32 is arranged outside the patient-accommodating region 14. In one embodiment, a camera may also to be arranged partly inside and partly outside the patient-accommodating region 14, as illustrated by camera 31. The pickup coil 40 that is connected to the radio frequency antenna control unit 21 is arranged on the radio frequency antenna unit 20 and may be configured to acquire characteristic RF parameters as positioning data.

The magnetic resonance unit 10 (e.g., the system control unit 22) further includes an analysis unit 26 that is configured to determine positioning information of the examination object 15 based on the acquired positioning data, an evaluation unit 27 that is configured to determine evaluation information based on the positioning information, and an output unit 28 that is configured to transmit an evaluation signal based on the evaluation information. The evaluation signal may be used, for example, to control a display on the display unit 24 and/or to control the gradient control unit 19 and/or the radio frequency antenna control unit 21.

For example, the system control unit 22 includes a programmable computation unit 30 including a memory that is not shown in greater detail. A computer program product may be loaded into the memory. The computer program product includes programming (e.g., instructions) in order to carry out a method for evaluating a positioning of the examination object 15 on the patient-positioning apparatus 16 of the magnetic resonance unit 10 if the program is run in the computation unit 30 of the magnetic resonance unit 10.

The magnetic resonance unit 10 shown in the present exemplary embodiment may include further components that magnetic resonance units usually have. A general mode of operation in a magnetic resonance unit 10 is known to the person skilled in the art, such that a detailed description of the general components may be dispensed with.

Figure 2:
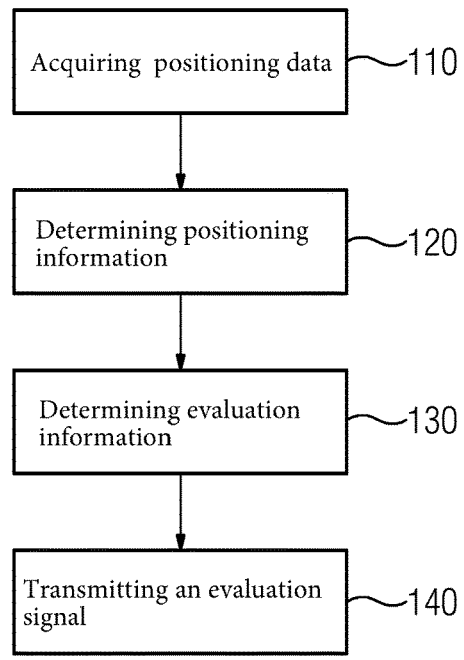
FIG. 2 shows a block representation of one embodiment of a method.

FIG. 2 illustrates by way of example a method according to one or more of the present embodiments for evaluating a positioning of an examination object on a patient-positioning apparatus in a magnetic resonance unit. In act 110, positioning data relating to the examination object is acquired with an acquisition unit, which includes, for example, the radio frequency antenna unit 20 and/or one or a plurality of cameras 31, 32, 33, 34 and/or one or a plurality of pickup coils 40.

With the cameras 31, 32, 33, 34, optical recognition of the patient 15 may be facilitated with the camera 32, for example, if the patient 15 is located on the patient table 17 outside the patient-accommodating region 14, and/or with the camera 31 when the patient table 17 is moved into the patient-accommodating region 14, and/or with the camera 33, 34 if the patient 15 is located inside the patient-accommodating region 14.

With the radio frequency antenna unit 20, in the course of an MRI procedure, possibly also while the patient table 17 is moving (e.g., is moving into the patient-accommodating region 14), positioning data may be acquired in the course of a magnetic resonance alignment. To detect patient movements during an MRI procedure, magnetic resonance signals may be acquired by the radio frequency antenna unit 20 as positioning data, and/or changed characteristic RF parameters that result from a potential change in the position of the patient 15 may be evaluated.

In act 120, positioning information relating to the examination object is determined by an analysis unit 26 based on the acquired positioning data. In one embodiment, the positioning information may be determined by a segmentation and/or a pattern recognition.

The positioning information may include contour information relating to at least one part of the examination object. For example, the contour information includes information about a relative position of at least two or of a plurality of parts of the body of the examination object 15.

Figure 4:
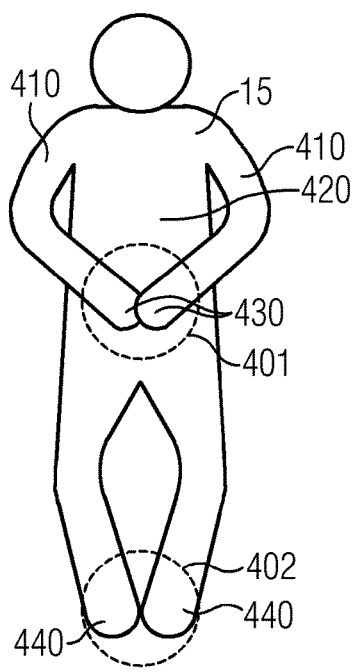
FIG. 4 shows a first representation of exemplary relative positions of a plurality of parts of the body.
Figure 5:
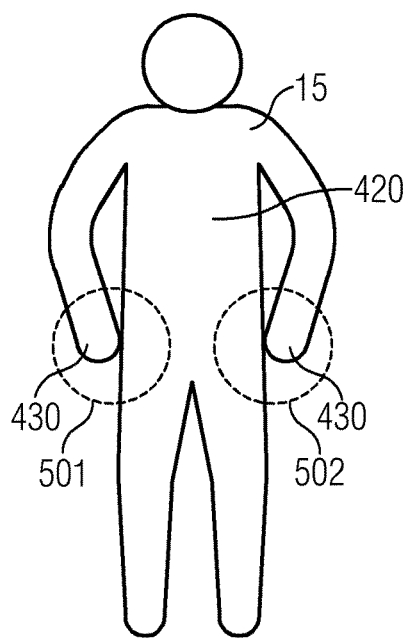
FIG. 5 shows a second representation of exemplary relative positions of a plurality of parts of the body.
Figure 6:
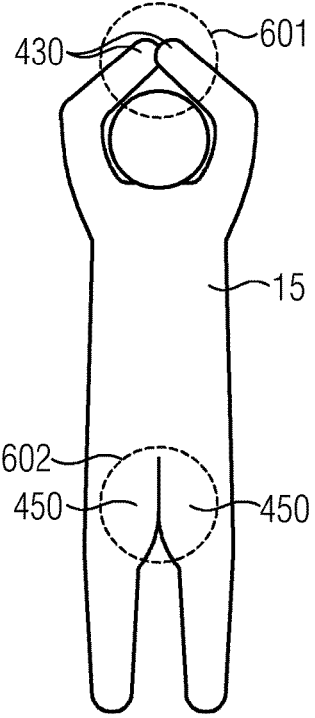
FIG. 6 shows a third representation of exemplary relative positions of a plurality of parts of the body.

Possible relative positions of the parts of the body of the examination object 15 are shown in FIGS. 4 to 6. Thus, FIG. 4 shows a patient 15 in a relative position 401, in which the hands 430 are touching, and in a further relative position 402, in which the feet 440 are touching.

FIG. 5 shows a patient 15 with two relative positions of parts of the body 501, 502, where the hands 430 are touching the upper body 420. In FIG. 6, the hands 430 are touching each other again in a relative position 601, and in a further relative position 602, the hands 430 are touching the thighs 450.

Among other things, the relative positions 401, 402, 501, 502, 601, 602 shown in FIGS. 4 to 6 are advantageously detected in order to avoid the relative positions 401, 402, 501, 502, 601, 602.

Figure 7:
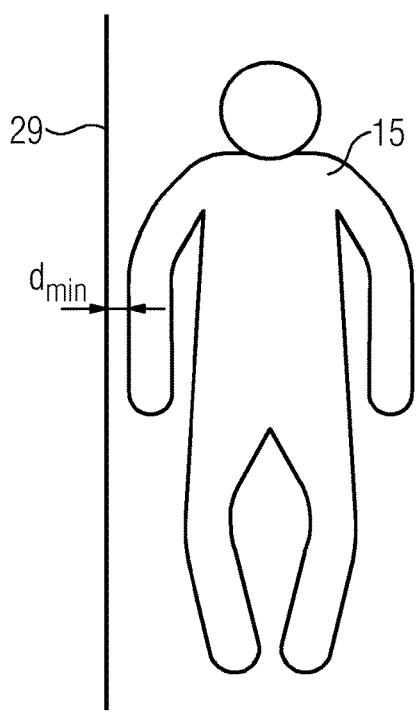
FIG. 7 shows a representation of an exemplary minimum distance between an examination object and an inside wall.

The positioning information advantageously includes positioning information relating to at least one part of the examination object 15 (e.g., a minimum distance $d_{min}$ between the examination object 15 and the inside wall 29 of the magnetic resonance unit 10), as shown in FIG. 7. If the distance $d_{min}$ is not critical, then a limiting value of a specific absorption rate to be monitored may be adjusted.

FIG. 2 further shows a further act 130, in which evaluation information is determined by the evaluation unit 27 using the positioning information. In an act 140, an evaluation signal is transmitted by the output unit 28, based on the evaluation information. The evaluation signal may include, for example, positive or negative release information. Negative release information may, for example, cause the system control unit 22 to refrain from switching on gradient pulses or excitation pulses.

Figure 3:
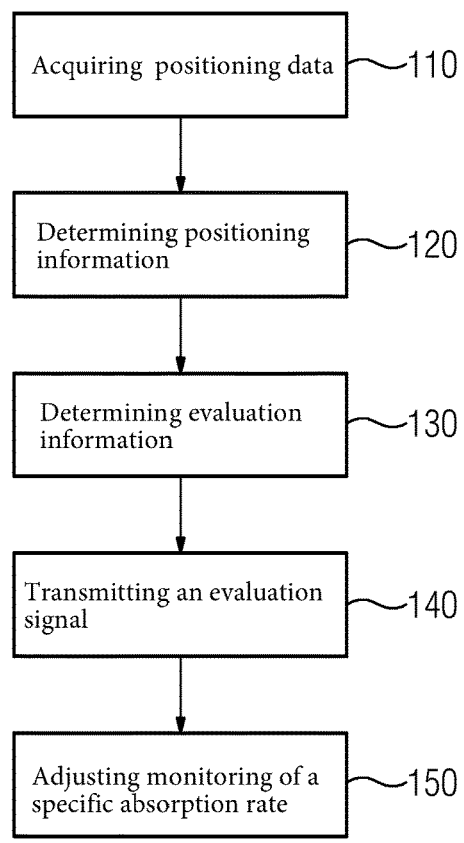
FIG. 3 shows a block diagram of one embodiment of an extended method.
Figure 8:
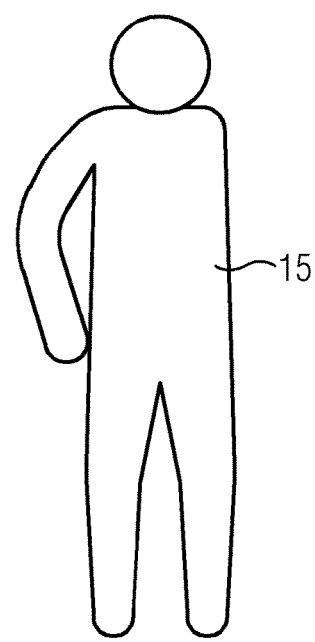
FIG. 8 shows a representation of an exemplary abnormal physiognomy of an examination object.

In FIG. 3, the method shown in FIG. 2 is extended by a further act 150, in which monitoring of a specific absorption rate is adjusted with the aid of the evaluation signal. The positioning information, for example, may include physiognomy information relating to at least one part of the examination object 15, where the monitoring of the specific absorption rate ensues as a function of the physiognomy information relating to the examination object 15. FIG. 8 shows, for example, an abnormal physiognomy of a patient 15, in which the patient has only one arm. By detecting that one arm is missing, a patient model that forms the basis of monitoring a specific absorption rate may be adjusted.

The methods described in detail above and also the magnetic resonance unit shown are merely exemplary embodiments that may be modified in a very wide variety of ways by a person skilled in the art without departing from the scope of the invention. The use of the indefinite article "a" or "an" does not preclude the relevant features from being present in plurality. The terms "unit" or "module" do not preclude the relevant components from consisting of a plurality of partial components that work in combination and may optionally also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for evaluating a positioning of an examination object on a patient-positioning apparatus in a magnetic resonance unit, the method comprising:
   acquiring, by an acquisition unit, positioning data relating to the examination object;
   determining, by an analysis unit, positioning information relating to the examination object using the acquired positioning data;
   determining, by an evaluation unit, evaluation information using the positioning information; and
   outputting, by an output unit, an evaluation signal using the evaluation information,
   wherein when the evaluation information indicates the examination object is in a correct position, the evaluation signal includes positive release information, and
   wherein when the evaluation information indicates the examination object is in an incorrect position, the evaluation signal includes negative release information.

2. The method of claim 1, wherein the positioning information includes contour information relating to at least one part of the examination object.

3. The method of claim 2, wherein the examination object includes a plurality of parts of a body, and
   wherein the contour information includes a relative position of at least two parts of the body of the plurality of parts of the body.

4. The method of claim 1, wherein the positioning information includes positioning information relating to at least one part of the examination object.

5. The method of claim 4, wherein the magnetic resonance unit includes a patient-accommodating region delimited by an inside wall, and
   wherein the positioning information includes a minimum distance between the examination object and the inside wall.

6. The method of claim 5, wherein when the minimum distance is not critical, a limiting value of a specific absorption rate to be monitored is adjustable.

7. The method of claim 1, wherein the positioning data relating to the examination object is acquired during a movement of the patient-positioning apparatus.

8. The method of claim 1, wherein the positioning data is acquired using optical signals acquired with at least one camera.

9. The method of claim 8, wherein the at least one camera is arranged outside a patient-accommodating region, inside the patient-accommodating region, inside a magnet unit, or any combination thereof.

10. The method of claim 1, wherein the positioning data is acquired using magnetic resonance signals.

11. The method of claim 1, wherein the positioning data relating to the examination object is acquired during capture of measurement data in a magnetic resonance scan.

12. The method of claim 1, wherein the positioning data is acquired using characteristic RF parameters.

13. The method of claim 1, wherein determining the positioning information comprises determining the positioning information using a segmentation, a pattern recognition, or the segmentation and the pattern recognition.

14. The method of claim 1, further comprising:
    monitoring a specific absorption rate; and
    adjusting the monitoring of the specific absorption rate with the aid of the evaluation signal.

15. The method of claim 14, wherein the positioning information includes physiognomy information relating to at least one part of the examination object, and
    wherein the monitoring of the specific absorption rate ensues as a function of the physiognomy information relating to the examination object.

16. A magnetic resonance unit comprising:
    an acquisition unit configured to acquire positioning data relating to an examination object;
    an analysis unit configured to determine positioning information relating to the examination object with the aid of the acquired positioning data;
    an evaluation unit configured to determine evaluation information using the positioning information; and
    an output configured to transmit an evaluation signal using the evaluation information,
    wherein when the evaluation information indicates the examination object is in a correct position, the evaluation signal includes positive release information, and
    wherein when the evaluation information indicates the examination object is in an incorrect position, the evaluation signal includes negative release information.

17. The magnetic resonance unit of claim 16, further comprising:
    a magnet unit, a patient-accommodating region and at least one camera,
    wherein the at least one camera is arranged outside the patient-accommodating region, inside the patient-accommodating region, inside the magnet unit, or any combination thereof.

18. The magnetic resonance unit of claim 16, wherein the magnetic resonance unit comprises at least one pickup coil.

19. A computer program product comprising a non-transitory computer-readable storage medium that stores instructions executable by a programmable computation unit of a magnetic resonance unit to evaluate a positioning of an examination object on a patient-positioning apparatus in a magnetic resonance unit, the instructions comprising:
- acquiring, by an acquisition unit, positioning data relating to the examination object;
- determining, by an analysis unit, positioning information relating to the examination object using the acquired positioning data;
- determining, by an evaluation unit, evaluation information using the positioning information; and
- outputting, by an output unit, an evaluation signal using the evaluation information,
- wherein when the evaluation information indicates the examination object is in a correct position, the evaluation signal includes positive release information, and
- wherein when the evaluation information indicates the examination object is in an incorrect position, the evaluation signal includes negative release information.

* * * * *